(12) United States Patent
Braun et al.

(10) Patent No.: US 8,685,636 B2
(45) Date of Patent: Apr. 1, 2014

(54) HEPARIN-INSENSITIVE METHOD FOR DETERMINING DIRECT COAGULATION FACTOR INHIBITORS

(75) Inventors: Konrad Braun, Ebsdorfergrund (DE); Wolfgang Klein, Marburg (DE); Norbert Zander, Marburg (DE); Michael Timme, Coelbe (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 14 days.

(21) Appl. No.: 13/366,746

(22) Filed: Feb. 6, 2012

(65) Prior Publication Data
US 2012/0202232 A1    Aug. 9, 2012

(30) Foreign Application Priority Data
Feb. 7, 2011  (EP) .................................... 11153524

(51) Int. Cl.
*A01N 1/02*    (2006.01)
*A61K 38/36*   (2006.01)

(52) U.S. Cl.
USPC ............................................ 435/2; 514/13.7

(58) Field of Classification Search
None
See application file for complete search history.

(56) References Cited

U.S. PATENT DOCUMENTS

| | | | |
|---|---|---|---|
| 4,234,682 A | 11/1980 | Bartl | |
| 4,409,327 A | 10/1983 | Bartl | |
| 4,440,678 A | 4/1984 | Svendsen | |
| 4,508,644 A | 4/1985 | Eberle | |
| 5,057,414 A * | 10/1991 | Stief et al. ...................... 435/13 |
| 5,262,325 A | 11/1993 | Heft | |
| 5,705,396 A | 1/1998 | Fickenscher | |
| 7,220,553 B2 * | 5/2007 | Chu .............................. 435/7.1 |

FOREIGN PATENT DOCUMENTS

| | | |
|---|---|---|
| EP | 0004271 | 10/1979 |
| EP | 0034122 | 8/1981 |
| EP | 0034320 | 5/1984 |
| EP | 0297597 | 1/1989 |
| EP | 0697463 | 2/1996 |
| WO | WO 9217187 | 10/1992 |

OTHER PUBLICATIONS

Ansell, Factor Xa or thrombin: is factor Xa a better target? Journal of Thrombosis and Haemostasis, 2007, 5 (Suppl. 1): 60-64.*
Schwienhorst, A., Direct thrombin inhibitors—a survey of recent developments, Cell. Mol. Life Sci, 63: 2773-2791 (2006).
Lange, U. et al. , A simple and specific assay for direct factor Xa inhibitors in plasma without interference by heparins. Posterabstract P17-05, Kongressausgabe Hämostaseologie (2010).
Samama, M.M. et al., Specific and rapid measurement of rivaroxaban using a new, dedicated chromogenic assay, Posterabstract P01-17, Kongressausgabe Hämostaseologie Jan. 2010.
Shechter, Y. et. al., Selective oxidation of methionine residues in proteins. Biochemistry, 14(20): 4497-4503, (1975).
EP Search Report dated Jun. 22, 2011 for Application No. 11153524.1.
EP Search Report dated Oct. 18, 2011 for Application No. 11153524.1.

* cited by examiner

*Primary Examiner* — Suzanne M Noakes
*Assistant Examiner* — Stephen Chong
(74) *Attorney, Agent, or Firm* — King & Spalding L.L.P.

(57) ABSTRACT

The invention is in the field of coagulation diagnostics and relates to a heparin-insensitive method for determining direct coagulation factor inhibitors in a sample, in particular direct thrombin and factor Xa inhibitors.

11 Claims, 1 Drawing Sheet

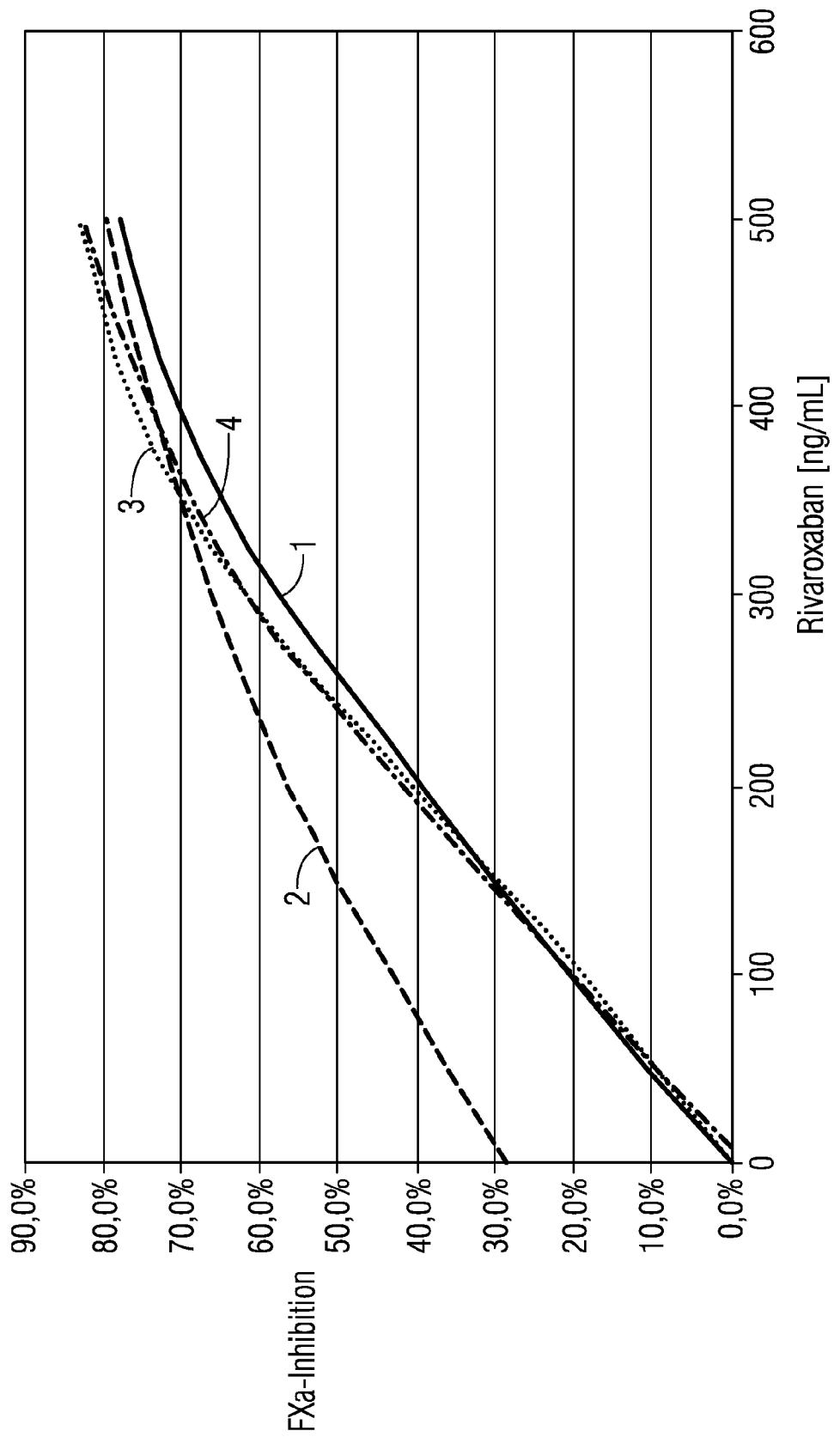

HEPARIN-INSENSITIVE METHOD FOR DETERMINING DIRECT COAGULATION FACTOR INHIBITORS

This application claims the benefit of European patent application no. EP11153524 filed on Feb. 7, 2011, the disclosure of which is incorporated, in its entirety, by this reference.

The present invention is in the field of coagulation diagnostics and relates to a heparin-insensitive method for determining direct coagulation factor inhibitors in a sample, in particular direct thrombin and factor Xa inhibitors, and to an assay kit for use in such a method.

In anticoagulation therapy, increasing use is made of novel direct coagulation inhibitors, in particular direct thrombin (factor IIa) and factor Xa inhibitors. Said novel coagulation inhibitors have the potential to supersede the indirect coagulation inhibitors used to date, especially heparin and derivatives thereof, which only develop their coagulation-inhibiting action in cooperation with cofactors such as antithrombin or heparin cofactor II. However, at present, the various heparins continue to be predominantly used.

The coagulation-inhibiting action of all heparins is based on their forming a complex with antithrombin (AT, antithrombin III), the most important plasmatic inhibitor of activated coagulation factors. Antithrombin is part of the group of serine protease inhibitors (serpins) and inhibits the coagulation factors thrombin (factor IIa, FIIa) and factor Xa (FXa) and also, to a slight extent, the other serine proteases FIXa, FXIa, FXIIa, kallikrein and plasmin. The binding of heparin to antithrombin results in a conformational change on the part of antithrombin, enhancing the inhibitory action of antithrombin many times over. The binding site in heparin molecules which is responsible for binding to antithrombin consists of a characteristic pentasaccharide sequence. A fully synthetic form of this pentasaccharide (fondaparinux) is, like UFH or LMWH, used for medicamentous inhibition of coagulation capacity.

Unfractionated heparins (UFHs) and fractionated heparins, heparin derivatives, heparinoids and pentasaccharides differ in their anticoagulatory action. Whereas UFHs inhibit thrombin and factor Xa equally, LMWHs mainly exhibit a factor Xa-inhibiting action and exhibit a thrombin-inhibiting action only to a lesser extent. Pentasaccharides such as fondaparinux selectively inhibit factor Xa and show no thrombin inhibition at all.

However, in certain pathological states, for example in the case of heparin-induced thrombocytopenia (HIT), treatment with heparin must be abandoned, and other anticoagulants, preferably direct thrombin and/or factor Xa inhibitors, must be administered to the patient. For these patients, it is necessary to have diagnostic methods available which enable an independent determination of the direct and indirect components of thrombin or factor Xa inhibition.

Thrombin and factor Xa inhibitors are usually determined using chromogenic assays. In these assays, the patient's sample, which contains a thrombin or factor Xa inhibitor, is mixed with a defined amount of the corresponding activated coagulation factor and with a chromogenic substrate for the activated coagulation factor, and the coagulation factor activity remaining in the reaction mix is measured photometrically. The higher the concentration of inhibitor in the patient's sample, the greater the inhibition of the activity of the coagulation factor added and the lower the measured activity in the reaction mix. EP 0034320 B1 or EP 0004271 A2, for example, describe such thrombin- or factor Xa-based chromogenic assays.

However, a disadvantage of this assay principle is that any kind of thrombin- or factor Xa-inhibiting activity is measured, without the possibility to distinguish whether, or to which extent, the inhibiting activity is caused by indirect or direct thrombin or factor Xa inhibitors.

In the prior art, this problem is solved by neutralizing or masking the inhibiting activity of heparin in assays in which thrombin or factor Xa inhibitors other than heparin are to be measured.

In a first known method, any heparins contained in the sample are degraded by the addition of heparin-degrading enzymes, for example heparinase, to the patient's sample. Heparinase activity leads to enzymatic degradation of heparin and all heparin derivatives which have a glycosaminoglycan sequence, and as a result, the indirect antithrombin-mediated inhibitory activity of heparin is eliminated. Other, direct thrombin or factor Xa inhibitors which do not have a glycosaminoglycan sequence are quantifiable after such pretreatment of the sample. This principle is described in U.S. Pat. No. 5,262,325.

In another known method for determining direct factor Xa inhibitors in the presence of heparin, a polyethylene glycol-conjugated factor Xa is added to the sample and the inhibition thereof is determined using a chromogenic substrate. Although polyethylene glycol-conjugated factor Xa is inhibitable by direct FXa inhibitors, for example rivaroxaban, it is not inhibitable by antithrombin-heparin complexes. The use of modified factor Xa therefore permits the specific determination of direct factor Xa inhibitors in the presence of heparin (Poster abstract P17-05, Lange, U. et al., A simple and specific assay for direct factor Xa inhibitors in plasma without interference by heparins. Conference edition of Hämostaseologie 1/2010).

In a further known method for determining direct factor Xa inhibitors in the presence of heparin, factor Xa and the inhibition thereof are determined using a chromogenic substrate in the presence of chaotropic substances. The chaotropic substances apparently prevent the antithrombin-heparin interaction, and so this method is also insensitive to the factor Xa-inhibiting action of heparins and therefore suitable for the specific determination of direct factor Xa inhibitors, for example rivaroxaban (Poster abstract P01-17, Samama, M. M. et al., Specific and rapid measurement of rivaroxaban using a new, dedicated chromogenic assay. Conference edition of Hämostaseologie 1/2010).

Further known methods for neutralizing heparin in patients' samples comprise the addition of polycations, such as hexadimethrine bromide (Polybrene®), or of metal salts, such as copper or zinc salts, whose ions form a complex with heparin (EP 0697463 A1).

It is an object of the present invention to provide a further method for specifically determining coagulation factor inhibitors which is insensitive to heparin and derivatives thereof and which can be readily automated in a coagulation measurement system.

The object is achieved by firstly mixing a sample suspected of containing heparin and one or more direct coagulation inhibitors with an oxidizing agent to form a reaction mix and carrying out an incubation thereof, and subsequently mixing the reaction mix with an agent which neutralizes the oxidizing agent. This prevents antithrombin-heparin interactions, and so the thrombin-inhibiting activity and the factor Xa-inhibiting activity of heparin are eliminated, and as a result, in subsequent determination of the inhibition of an added activated coagulation factor, such as thrombin or factor Xa, only the inhibiting effect of direct coagulation inhibitors is specifically measured.

The present invention thus provides a method for determining a direct inhibitor of a coagulation factor in a sample, wherein the method comprises the following steps:
a) mixing the sample with an oxidizing agent to form a reaction mix;
b) incubating the reaction mix;
c) mixing the reaction mix with an agent which neutralizes the oxidizing agent;
d) adding a defined amount of the activated coagulation factor to the reaction mix;
e) determining the inhibition of the activated coagulation factor added.

The term "direct inhibitor of a coagulation factor" or "direct anticoagulant" relates to nonphysiological, preferably therapeutically active substances which reduce the activity of the coagulation factor by direct interaction with the coagulation factor. Direct inhibitors of coagulation factors, for the determination of which the method according to the invention is suitable, are in particular direct inhibitors of the coagulation factor thrombin, for example hirudin, dabigatran, melagatran, argatroban, ximelagatran, bivalirudin, lepirudin, MCC-977, SSR-182289, TGN-255, TGN-167, ARC-183 and odiparcil, or direct inhibitors of the coagulation factor Xa, for example rivaroxaban, apixaban, otamixaban (which are grouped under the xabans, a novel class of drugs), LY 517717, YM 153, DU-176b, DX-9065a and KFA-1982.

Direct inhibitors should be distinguished from "indirect inhibitors" or "indirect anticoagulants", which reduce the activity of a coagulation factor only by interaction with physiological cofactors, for example antithrombin or heparin cofactor II. Indirect inhibitors of coagulation factors, to which the method according to the invention is insensitive, are in particular heparins and heparin-like substances which have at least one glycosaminoglycan sequence, for example unfractionated high-molecular-weight heparins (HMWHs, UFHs), fractionated low-molecular-weight heparins (LMWHs), heparin derivatives and heparinoids. Heparin derivatives and heparinoids are enzymatically and/or chemically modified glycosaminoglycan chains whose anticoagulatory properties may be biotechnologically modified by the specific manipulation of glycan chain length, sulfation or acetylation pattern or the mixture of different glycosaminoglycans, for example, in the case of danaparoid sodium, a mixture of glycosaminoglycans which consists mainly of heparan sulfate and, to a lesser extent, of dermatan sulfate and chondroitin sulfate. Synthetic heparins, such as the pentasaccharide fondaparinux, also have an indirect effect via antithrombin. For the purposes of the present invention, the term "heparin" comprehends hereinafter all aforementioned heparins, heparinoids and heparin derivatives.

The term "oxidizing agent" comprehends substances which bring about the oxidation of sterically relevant amino acids of plasmatic serine protease inhibitors, in particular antithrombin. Oxidation of sterically relevant amino acids prevents the formation of the active conformation of the serine protease inhibitor and thus the inhibition of the active site of serine proteases such as factor Xa or factor IIa. Preferred oxidizing agents are, for example, hypochlorites and salts thereof, for example sodium or potassium hypochlorite, which are active in the neutral pH range. This has the advantage that the analytes to be assayed, the direct coagulation factor inhibitors, are not degraded owing to extreme pH values of the reaction mix. In many cases, methionine is involved in the formation of sterically relevant conformations in serine protease inhibitors. Other preferred oxidizing agents are therefore substances from the group consisting of reactive halogens, hydrogen peroxides, peroxymonosulfuric acid, peroxydisulfuric acid, chloramine B, chloramine T, hypochlorous acid, N-chlorosuccinimide or salts of the above-listed substances, which oxidize methionine to give methionine sulfoxide and thus block serine protease inhibitor activity (see also Shechter, Y. et. al., Selective oxidation of methionine residues in proteins. Biochemistry 1975, 14(20), 4497-4503).

The term "agent which neutralizes the oxidizing agent" comprehends substances which neutralize the oxidative activity of the oxidizing agent used, i.e., nullify it, and so the latter cannot cause any further interferences which may affect the measurement principle. A suitable agent which neutralizes the oxidative activity of the oxidizing agent is a mild reducing agent. In the simplest case, a halogen acid suffices for this purpose, preferably low-molar aqueous solutions of chlorine acids, for example hydrochloric acid, which destabilizes the oxidizing agent, and so both components can react to completion in the aqueous system. Alternatively, use can also be made of fructose, polyols, fruit acids and salts thereof. Not suitable are all stronger reducing agents, for example boric acid, which could interfere with subsequent reaction steps.

A "sample" is, for the purposes of the invention, understood to mean the material which is suspected of containing the direct coagulation inhibitor to be determined. The term sample comprehends in particular human or animal body fluids, especially blood, plasma and serum.

The method according to the invention for determining a direct inhibitor of a coagulation factor comprises, inter alia, the mixing of the sample with an oxidizing agent to form a reaction mix, which is then incubated for a finite period before an agent which neutralizes the oxidizing agent is added to the reaction mix.

The duration of incubation of the reaction mix after addition of the oxidizing agent should be at least 30 seconds before the neutralizing agent is added. Preferably, the reaction mix is incubated for a period of about 30 to 180 seconds, particularly preferably for a period of 90 to 120 seconds.

The sample pretreated in this way is then subjected to a conventional coagulation factor activity assay, wherein a defined amount of the activated coagulation factor for which the direct coagulation inhibitor to be determined is specific is added to the sample pretreated according to the invention. Consequently, in the case of a method for determining a direct thrombin inhibitor, a defined amount of thrombin is added; in the case of a method for determining a direct factor Xa inhibitor, a defined amount of factor Xa is added, and the inhibitor-dependent inactivation of the activity of the coagulation factor added is measured. Preferably, the inhibitor-dependent inactivation of the amidolytic activity of the coagulation factor added is determined using a chromogenic, fluorogenic or differently labeled substrate which is specifically cleaved by the activated coagulation factor. The cleavable signal group of a substrate can be, for example, a dye determinable in the visible range of the spectrum, a fluorescent dye, or a dye determinable in the UV range. Preferably, use is made of peptides which have on the carboxy group of an arginine residue a chromophore bound via an amide bond. Particularly suitable for this purpose are p-nitroanilide (pNA) groups and 5-amino-2-nitrobenzoic acid (ANBA) derivatives, and also dyes derived therefrom by substitution, which can be quantified by photometric measurement at a wavelength of 405 nm after removal from the peptide portion. Preferably, the peptide portion of a cleavable substrate consists of 3 to about 150 amino acid residues. Patent documents EP 0034122 A1 and U.S. Pat. No. 4,508,644 describe a multiplicity of suitable chromogenic peptide substrates, the preparation thereof and the use thereof in coagulation diagnostic assays, for example for determining the coagulation factors factor IIa (thrombin) and factor Xa.

The amount of signal-producing cleavage product released, for example of the chromogenic, fluorogenic or amperogenic group, is inversely proportional to the inhibitor activity or concentration in the sample. Using a calibration curve generated from the measurement of samples having known inhibitor activities, it is possible to correctly quantify the amount of a direct coagulation inhibitor in a patient's sample.

Amidolytic activity can be evaluated kinetically or as end-point determination. In the case of the kinetic method, the reaction, i.e., the remaining coagulation factor activity as a measure of the inhibitor activity present, is quantified on the basis of the reaction rate for the cleavable substrate. In the case of end-point determination, the cleavage reaction is stopped after a predetermined measurement time and the amount of cleavage product released is measured.

A particular advantage of the method according to the invention is that it differs from a conventional method for determining heparin activity in a sample only in the pretreatment of the sample and can therefore be combined outstandingly well with such a method. It is thus, for example, possible to mix each of a first aliquot of a sample, and a second aliquot of the same sample which, according to the invention, has been mixed firstly with an oxidizing agent and subsequently with an agent which neutralizes the oxidizing agent, with a first reagent containing a defined concentration of an activated coagulation factor and with a second reagent containing a coagulation factor-specific substrate, and to determine the inhibitor-dependent inactivation of the activity of the coagulation factor added The assay result of the first, untreated aliquot reflects the overall anticoagulatory potential, i.e., the sum of all coagulation factor-inhibiting activities of the sample, including any heparin activities. By contrast, the assay result of the second aliquot, which has been pretreated according to the invention, specifically reflects the coagulation factor-inhibiting activities of any direct coagulation factor inhibitors in the sample.

A further aspect of the present invention relates to an assay kit for carrying out the method according to the invention for determining a direct inhibitor of a coagulation factor in a sample, wherein the assay kit contains at least two reagents, of which one contains an oxidizing agent and the other contains an agent which neutralizes the oxidizing agent. The reagents may additionally contain preservatives and be provided either as liquid reagents or as lyophilisates. A preferred assay kit contains a first reagent containing sodium hypochlorite as oxidizing agent, and a second reagent containing hydrochloric acid as neutralizing agent.

An assay kit according to the invention preferably additionally contains further reagents, particularly preferably a reagent which contains an activated coagulation factor, preferably thrombin or factor Xa, and/or a reagent which contains a substrate for the activated coagulation factor, which substrate has a detectable signal group.

The reagents of the assay kit according to the invention may be provided in liquid or lyophilized form. If some or all reagents of the assay kit are present as lyophilisates, the assay kit may additionally contain the solvents required to dissolve the lyophilisates, for example distilled water, suitable buffers and/or standard human plasma.

BRIEF DESCRIPTION OF THE DRAWINGS

FIG. 1

Determination of rivaroxaban-specific factor Xa inhibition in heparin-containing samples (see example 2).

Curve 1: rivaroxaban containing plasmas without heparin (R0 to R5), without pretreatment according to the invention;

Curve 2: rivaroxaban containing plasmas with heparin (R0H to R5H), without pretreatment according to the invention; the inhibition measured is the sum of rivaroxaban and heparin inhibition;

Curve 3: rivaroxaban containing plasmas without heparin (R0 to R5), with pretreatment according to the invention;

Curve 4: rivaroxaban containing plasmas with heparin (R0H to R5H), with pretreatment according to the invention; the inhibition measured corresponds to rivaroxaban inhibition (cf. curve 1 or 3); heparin inhibition has been eliminated by the pretreatment according to the invention.

EXAMPLES

The following exemplary embodiments serve to illustrate the invention and are not to be understood as limiting.

Example 1

Elimination of Heparin Activity in Samples by Adding an Oxidizing Agent and a Neutralizing Agent Example 1a)

Determination of a Direct Factor Xa Inhibitor in Samples Pretreated According to the Invention Various amounts of direct coagulation factor inhibitors (rivaroxaban as direct factor Xa inhibitor, argatroban as direct thrombin inhibitor) or indirect coagulation factor inhibitors (fondaparinux pentasaccharide [Arixtra®], high-molecular-weight heparin [HMWH]) were added to normal human plasma.

20 µl of plasma sample were mixed with 10 µl of a 0.1% strength hypochlorous acid (sodium hypochlorite) as oxidizing agent, and the reaction mix was incubated at +37° C. for 30 seconds. Subsequently, 10 µl of a 0.1% strength hydrochloric acid solution were added to the reaction mix to neutralize the oxidizing agent, and the reaction mix was incubated at +37° C. for 30 seconds. Subsequently, 95 µl of factor Xa reagent (human factor Xa, 1 U/ml in TRIS buffer, pH 8.0) were added to the reaction mix, and the reaction mix was incubated at +37° C. for 30 seconds. Subsequently, 80 µl of a chromogenic factor Xa substrate (Z-D-Leu-Gly-Arg-ANBA-methylamide, 4 mmol/l) were added to the reaction mix, and conversion of the substrate (in ΔA/time) was determined at a wavelength of 405 nm in an automated coagulation measurement instrument (BCS® System, Siemens Healthcare Diagnostics).

The reduction in substrate conversion compared to plasma without any inhibitors correlates with the amount of inhibitor in the sample.

The results are shown in table 1. Pretreatment of the samples in accordance with the invention brings about an almost complete elimination of the inhibition of factor Xa by indirect inhibitors such as Arixtra (fondaparinux) or high-molecular-weight heparin. However, the factor Xa-inhibiting action of direct inhibitors such as rivaroxaban is not impaired by pretreatment of the samples in accordance with the invention. In samples containing a direct thrombin inhibitor (argatroban), factor Xa inhibition does not take place anyway.

TABLE 1

| Plasma | | ΔA/min | FXa inhibition |
|---|---|---|---|
| Without inhibitor | | 2268 | 0% |
| With direct inhibitor | 200 ng/ml rivaroxaban | 1296 | 43% |
| | 20 μg/ml argatroban | 2176 | 4% |
| With indirect inhibitor | 1 μg/ml Arixtra | 2319 | 4% |
| | 4 μg/ml Arixtra | 2344 | 3% |
| | 0.5 U/ml heparin | 2353 | 4% |
| | 2.0 U/ml heparin | 2283 | 1% |

Example 1b)

Determination of a Direct Thrombin Inhibitor in Samples Pretreated According to the Invention 20 μl of plasma sample were mixed with 10 μl of a 0.1% strength hypochlorous acid (sodium hypochlorite) as oxidizing agent, and the reaction mix was incubated at +37° C. for 30 seconds. Subsequently, 10 μl of a 0.1% strength hydrochloric acid solution were added to the reaction mix to neutralize the oxidizing agent, and the reaction mix was incubated at +37° C. for 30 seconds. Subsequently, 140 μl of thrombin reagent (bovine thrombin, 6 U/ml) were added to the reaction mix, and the reaction mix was incubated at +37° C. for 30 seconds. Subsequently, 50 μl of a chromogenic thrombin substrate (Tos-L-Gly-Pro-Arg-ANBA-isopropylamide, 4 mmol/l) were added to the reaction mix, and conversion of the substrate (in ΔA/time) was determined at a wavelength of 405 nm in an automated coagulation measurement instrument (BCS® System, Siemens Healthcare Diagnostics).

The reduction in substrate conversion compared to plasma without any inhibitors correlates with the amount of inhibitor in the sample.

The results are shown in table 2. Pretreatment of the samples in accordance with the invention brings about an almost complete elimination of the inhibition of thrombin by indirect inhibitors such as Arixtra (fondaparinux) or high-molecular-weight heparin. However, the thrombin-inhibiting action of direct inhibitors such as argatroban is not impaired by pretreatment of the samples in accordance with the invention. In samples containing a direct factor Xa inhibitor (rivaroxaban), thrombin inhibition does not take place anyway.

TABLE 2

| Plasma | | ΔA/min | Thrombin inhibition |
|---|---|---|---|
| Without inhibitor | | 2623 | 0% |
| With direct inhibitor | 200 ng/ml rivaroxaban | 2612 | 0% |
| | 20 μg/ml argatroban | 140 | 95% |
| | 200 μg/ml argatroban | 36 | 99% |
| With indirect inhibitor | 1 μg/ml Arixtra | 2480 | 5% |
| | 4 μg/ml Arixtra | 2579 | 2% |
| | 0.5 U/ml heparin (HMW) | 2533 | 3% |
| | 2.0 U/ml heparin (HMW) | 2594 | 1% |

Example 2

Specific Determination of the Direct Factor Xa Inhibitor Rivaroxaban in Heparin-Containing Samples Various amounts of the direct factor Xa inhibitor rivaroxaban, or various amounts of the direct factor Xa inhibitor rivaroxaban and various amounts of the indirect factor Xa inhibitor heparin (HMWH), were added to normal human plasma (see table 3).

TABLE 3

| | Sample | | | | | | | | | | | |
|---|---|---|---|---|---|---|---|---|---|---|---|---|
| | R0 | R1 | R2 | R3 | R4 | R5 | R0H | R1H | R2H | R3H | R4H | R5H |
| Rivaroxaban (ng/ml) | 0 | 100 | 200 | 300 | 400 | 500 | 0 | 100 | 200 | 300 | 400 | 500 |
| Heparin (U/ml) | 0 | 0 | 0 | 0 | 0 | 0 | 0.4 | 0.4 | 0.4 | 0.4 | 0.4 | 0.4 |

9 μl of plasma sample were mixed first with 6 μl of water and then with 8 μl of a 0.1% strength hypochlorous acid (sodium hypochlorite) as oxidizing agent, and heated to +37° C. Subsequently, 8 μl of a 0.1% strength hydrochloric acid solution were added to the reaction mix to neutralize the oxidizing agent, and the reaction mix was incubated at +37° C. for 120 seconds. Subsequently, 150 μl of factor Xa reagent (human factor Xa, 1 U/ml in TRIS buffer, pH 8.0) were added to the reaction mix, and the reaction mix was incubated at +37° C. for 120 seconds. Subsequently, 30 μl of a chromogenic factor Xa substrate (Z-D-Leu-Gly-Arg-ANBA-methylamide, 4 mmol/l) were added to the reaction mix, and conversion of the substrate (in ΔA/time) was determined at a wavelength of 405 nm in an automated coagulation measurement instrument (BCS® System, Siemens Healthcare Diagnostics).

In parallel, the samples without the pretreatment according to the invention with 0.1% strength hypochlorous acid and with 0.1% strength hydrochloric acid solution were assayed using the above-described method.

The reduction in substrate conversion compared to plasma without any inhibitors correlates with the amount of inhibitor in the sample.

The results are shown in FIG. 1. Pretreatment of samples containing rivaroxaban and heparin in accordance with the invention has the effect that only factor Xa inhibition which corresponds to factor Xa inhibition by rivaroxaban is measured (compare curve 2, without pretreatment, and curve 4, with pretreatment). Therefore, the method according to the invention permits the specific determination of rivaroxaban activity in heparin-containing samples.

The invention claimed is:

1. A method for determining a direct inhibitor of a coagulation factor in a sample, wherein the method comprises the following steps performed in the following order:
   a) mixing the sample with an oxidizing agent to form a reaction mix;
   b) incubating the reaction mix;
   c) mixing the reaction mix with an agent which neutralizes the oxidizing agent;
   d) adding a defined amount of an activated coagulation factor to the reaction mix; and
   e) determining the inhibition of the activated coagulation factor added; and
   wherein the method is heparin-insensitive.

2. The method as claimed in claim 1, wherein, in step a), the sample is mixed with an oxidizing agent selected from the group consisting of hypochlorites and salts thereof, sodium or potassium hypochlorite, reactive halogens, hydrogen peroxides, peroxymonosulfuric acid, peroxydisulfuric acid, chloramine B, chloramine T, hypochlorous acid, and N-chlorosuccinimide and salts thereof.

3. The method as claimed in claim 1, wherein, in step c), the reaction mix is mixed with a neutralizing agent selected from the group consisting of halogen acids, low-molar aqueous solutions of chlorine acids hydrochloric acid; fructose; and polyols.

4. The method as claimed in claim 1, wherein the duration of incubation in step b) is at least about 30 seconds.

5. The method as claimed in claim 1, wherein the activated coagulation factor is thrombin.

6. The method as claimed in claim 5 wherein the direct inhibitor is a direct thrombin inhibitor selected from the group consisting of hirudin, dabigatran, melagatran, argatroban, ximelagatran, bivalirudin, lepirudin, MCC-977, SSR-182289, TGN-255, TGN-167, ARC-183 and odiparcil.

7. The method as claimed in claim 1, wherein the activated coagulation factor is factor Xa.

8. The method as claimed in claim 7 wherein the direct inhibitor a direct factor Xa inhibitor selected from the group consisting of rivaroxaban, apixaban, otamixaban, LY 517717, YM 153, DU-176b, DX-9065a and KFA-1982.

9. The method as claimed in claim 1, wherein, after step c), a chromogenic, fluorogenic or differently labeled substrate which is specifically cleaved by the activated coagulation factor is also added to the reaction mix and the amount of signal-producing cleavage product released is measured.

10. The method as claimed in claim 4, wherein the duration of incubation in step b) is about 30 to 180 seconds.

11. The method as claimed in claim 4, wherein the duration of incubation in step b) is about 90 to 120 seconds.

* * * * *